United States Patent
Stapf et al.

(10) Patent No.: US 12,069,437 B2
(45) Date of Patent: Aug. 20, 2024

(54) DIRECT INFORMATIVE COMMUNICATION THROUGH AN EAR-WEARABLE DEVICE

(71) Applicant: Starkey Laboratories, Inc., Eden Prairie, MN (US)

(72) Inventors: Michael D. Stapf, Prior Lake, MN (US); Collin Steven Jasnoch, Savage, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 213 days.

(21) Appl. No.: 17/621,580

(22) PCT Filed: Jun. 25, 2020

(86) PCT No.: PCT/US2020/039677
§ 371 (c)(1),
(2) Date: Dec. 21, 2021

(87) PCT Pub. No.: WO2020/264203
PCT Pub. Date: Dec. 30, 2020

(65) Prior Publication Data
US 2022/0360913 A1 Nov. 10, 2022

Related U.S. Application Data

(60) Provisional application No. 62/868,071, filed on Jun. 28, 2019.

(51) Int. Cl.
*H04R 25/00* (2006.01)
*A61B 5/00* (2006.01)

(52) U.S. Cl.
CPC ......... *H04R 25/554* (2013.01); *A61B 5/0026* (2013.01); *A61B 5/746* (2013.01); *H04R 2225/55* (2013.01)

(58) Field of Classification Search
CPC .......................... H04R 25/554; H04R 2225/55
See application file for complete search history.

(56) References Cited

U.S. PATENT DOCUMENTS

| 2,547,122 A | 4/1951 | Heston |
| 7,062,223 B2 | 6/2006 | Gerber et al. |

(Continued)

FOREIGN PATENT DOCUMENTS

| EP | 2547122 | 1/2013 |
| EP | 2735845 | 5/2014 |
| WO | 2020264203 | 12/2020 |

OTHER PUBLICATIONS

"International Preliminary Report on Patentability," for PCT Application No. PCT/US2020/039677 mailed Jan. 6, 2022 (8 pages).

(Continued)

*Primary Examiner* — Suhan Ni
(74) *Attorney, Agent, or Firm* — Pauly, DeVries Smith & Deffner LLC (57) ABSTRACT

A method and system are described for providing high-priority notification messages to a user of an ear-wearable device system. The ear-wearable device system includes a physiological sensor present on, within, or carried with the user and an ear-wearable device comprising a speaker, a microphone, a processor, a memory storage, and a wireless communication device. The system is capable of receiving a plurality of sensor messages from the physiological sensor, identifying high-priority sensor information from among the plurality of received sensor messages, identifying content for an audio voice message to provide to the user, and providing the audio voice message at the speaker of the ear-wearable device. The content includes user notification information containing or based on the high-priority sensor information identified from among the received sensor messages.

20 Claims, 7 Drawing Sheets

(56) References Cited

U.S. PATENT DOCUMENTS

| | | |
|---|---|---|
| 7,920,907 B2 | 4/2011 | McGarraugh et al. |
| 8,461,986 B2 | 6/2013 | Snyder |
| 9,167,356 B2 | 10/2015 | Higgins et al. |
| 9,452,259 B2 | 9/2016 | Dobbles et al. |
| 9,867,539 B2 | 1/2018 | Heikenfeld et al. |
| 10,136,831 B2 | 11/2018 | Heikenfeld |
| 2007/0133756 A1 | 6/2007 | Graves et al. |
| 2009/0221888 A1 | 9/2009 | Wijesiriwardana |
| 2009/0224932 A1 | 9/2009 | Kilim et al. |
| 2011/0068915 A1 | 3/2011 | Wakefield |
| 2013/0343585 A1 | 12/2013 | Bennett et al. |
| 2014/0172831 A1 | 6/2014 | Jin et al. |
| 2015/0057515 A1 | 2/2015 | Hagen et al. |
| 2015/0172831 A1 | 6/2015 | Dittberner et al. |
| 2017/0172484 A1 | 6/2017 | Sonner et al. |
| 2018/0035928 A1 | 2/2018 | Sonner et al. |
| 2018/0263538 A1 | 9/2018 | Heikenfeld et al. |
| 2018/0277238 A1 | 9/2018 | Boesen |
| 2018/0341582 A1 | 11/2018 | Moon et al. |
| 2018/0344223 A1 | 12/2018 | Heikenfeld |
| 2019/0041345 A1 | 2/2019 | Nogueira et al. |
| 2019/0059795 A1 | 2/2019 | Heikenfeld |
| 2019/0122125 A1 | 4/2019 | Dragicevic et al. |

OTHER PUBLICATIONS

"International Search Report and Written Opinion," for PCT Application No. PCT/US2020/039677 mailed Sep. 16, 2020 (12 pages).

DIRECT INFORMATIVE COMMUNICATION THROUGH AN EAR-WEARABLE DEVICE

This application is being filed as a PCT International Application on Jun. 25, 2020 in the name of Starkey Laboratories, Inc., a U.S. national corporation, applicant for the designation of all countries and Michael D. Stapf, a U.S. Citizen, and Collin Steven Jasnoch, a U.S. Citizen, inventors for the designation of all countries, and claims priority to U.S. Provisional Patent Application No. 62/868,071, filed Jun. 28, 2019, the contents of which is hereby incorporated by reference in its entirety.

FIELD

Embodiments herein relate to systems and methods using an ear-wearable device, such as a hearing aid, to deliver notifications to a user.

BACKGROUND

Many electronic devices provide notification messages to users, and these notifications may originate from games, email, news sources, cell phone calls, text messaging applications, and other sources. The quantity of messages that many users are exposed to can leave them feeling overwhelmed and can result in important messages being ignored. Often, obtaining the full content of the notification message from these traditional sources requires user interaction, such as unlocking a cell phone, activating an application on the cell phone, and/or pressing a physical button on a device paired with a cell phone. The user may not take that next step to view the full content of the notification, and as a result, may not receive the intended notification. The user may also be physically distracted from another activity, such as driving, in order to take that next step to view the full content of the notification.

In some systems today, time-sensitive notifications are intermixed with low priority notifications. As a result, the time-sensitive information can be lost in the collections of all notifications. Some systems offer user customization for various notification, such as custom ring tones or chimes for information from specific applications. These systems require user set-up and rely on the user remembering the meanings assigned to various ring tones and chimes.

SUMMARY

In a first aspect, a method provides high-priority notification messages to a user of an ear-wearable device system. The ear-wearable device system includes a physiological sensor present on, within, or carried with the user. An ear-wearable device can include a speaker, a microphone, a processor, a memory storage, and a wireless communication device. The method includes: receiving a plurality of sensor messages from the physiological sensor; identifying high-priority sensor information from among the plurality of received sensor messages; identifying content for an audio voice message to provide to the user, wherein the content includes user notification information containing or based on the high-priority sensor information identified from among the received sensor messages; and providing the audio voice message at the speaker of the ear-wearable device.

In a second aspect, in addition to one or more of the preceding or following aspects, or in the alternative to some aspects, the physiological sensor is located within a housing of the ear-wearable device.

In a third aspect, in addition to one or more of the preceding or following aspects, or in the alternative to some aspects, the physiological sensor includes a sensor housing separate from a housing of the ear-wearable device.

In a fourth aspect, in addition to one or more of the preceding or following aspects, or in the alternative to some aspects, the physiological sensor is a glucose sensor, a blood glucose sensor, a dehydration sensor, a temperature sensor, an inertial motion unit sensor, a gyroscope, an inertial measurement unit (IMU), a respiration rate sensor, an electrocardiogram sensor, a hormonal sensor, a fertility sensor, a blood pressure sensor, a peripheral capillary oxygen saturation sensor, a chemical sensor, a chemical blood sensor, a drug sensor, a voice pattern sensor, a stomach acidity sensor, a cholesterol level sensor, an implanted sensor, a pacemaker, or an electronic pill.

In a fifth aspect, in addition to one or more of the preceding or following aspects, or in the alternative to some aspects, the plurality of sensor messages are received by a processor of the ear-wearable device.

In a sixth aspect, in addition to one or more of the preceding or following aspects, or in the alternative to some aspects, the ear-wearable device system further includes a gateway device. The gateway device can include a processor, a wireless communication device for communicating with the ear-wearable device, and a second wireless communication device for communicating with a pervasive wireless network. The plurality of sensor messages are received by the processor of the gateway device.

In a seventh aspect, in addition to one or more of the preceding or following aspects, or in the alternative to some aspects, the method further can include: sending the plurality of sensor messages to a data warehouse location; analyzing the plurality of sensor messages received at the data warehouse location for trends using analysis techniques; performing machine learning training to improve the analysis techniques used to analyze the plurality of sensor messages received at the data warehouse location; receiving, at the data warehouse location, first input from the user of the ear-wearable device system; and applying first input to improve the analysis techniques.

In an eighth aspect, in addition to one or more of the preceding or following aspects, or in the alternative to some aspects, the method further can include: identifying supplemental data from a supplemental data source relevant to the high-priority sensor information, wherein the content for the audio voice message includes supplemental data notification information containing or based on the supplemental data.

In a ninth aspect, in addition to one or more of the preceding or following aspects, or in the alternative to some aspects, the supplemental data is geo-location data and the supplemental data source is a global positioning system.

In a tenth aspect, in addition to one or more of the preceding or following aspects, or in the alternative to some aspects, the supplemental data is directions to a location relevant to the high-priority sensor information.

In an eleventh aspect, in addition to one or more of the preceding or following aspects, or in the alternative to some aspects, the supplemental data source is a gateway device, a global positioning system, a calendar system, a personal contact information system, a contact directory system, a second physiological sensor, a database of user-selected parameters, a database of environmental information, a glucose sensor, a blood glucose sensor, a dehydration sensor, a temperature sensor, an inertial motion unit sensor, a gyroscope, an inertial measurement unit (IMU), a respiration rate sensor, an electrocardiogram sensor, a hormonal sensor, a fertility sensor, a blood pressure sensor, a peripheral capillary oxygen saturation sensor, a chemical sensor, a chemical blood sensor, a drug sensor, a voice pattern sensor, a stomach acidity sensor, a cholesterol level sensor, an implanted sensor, a pacemaker, or an electronic pill.

In a twelfth aspect, an ear-wearable device system capable of providing high-priority notification messages to a user, is included having a physiological sensor present on, within, or carried with the user. The system also includes an ear-wearable device that can include a speaker, a microphone, a processor, a memory storage, and a wireless communication device. The processor is capable of: receiving a plurality of sensor messages from the physiological sensor; identifying high-priority sensor information from among the plurality of received sensor messages; identifying content for an audio voice message to provide to the user, wherein the content includes user notification information containing or based on the high-priority sensor information identified from among the received sensor messages; and providing the audio voice message at the speaker of the ear-wearable device.

In a thirteenth aspect, in addition to one or more of the preceding or following aspects, or in the alternative to some aspects, the physiological sensor is located within a housing of the ear-wearable device.

In a fourteenth aspect, in addition to one or more of the preceding or following aspects, or in the alternative to some aspects, the physiological sensor includes a sensor housing separate from a housing of the ear-wearable device.

In a fifteenth aspect, in addition to one or more of the preceding or following aspects, or in the alternative to some aspects, the physiological sensor is a glucose sensor, a blood glucose sensor, a dehydration sensor, a temperature sensor, an inertial motion unit sensor, a gyroscope, an inertial measurement unit (IMU), a respiration rate sensor, an electrocardiogram sensor, a hormonal sensor, a fertility sensor, a blood pressure sensor, a peripheral capillary oxygen saturation sensor, a chemical sensor, a chemical blood sensor, a drug sensor, a voice pattern sensor, a stomach acidity sensor, a cholesterol level sensor, an implanted sensor, a pacemaker, or an electronic pill.

In a sixteenth aspect, an ear-wearable device system capable of providing high-priority notification messages to a user includes a physiological sensor present on, within, or carried with the user. The system also includes an ear-wearable device which can include a speaker, a microphone, a processor, a memory storage, and a wireless communication device; and a gateway device. The gateway device can include a processor, a wireless communication device for communicating with the ear-wearable device, and a second wireless communication device for communicating with a pervasive wireless network. The processor of the ear-wearable device or the processor of the gateway device is configured for: receiving a plurality of sensor messages from the physiological sensor; identifying high-priority sensor information from among the plurality of received sensor messages; identifying content for an audio voice message to provide to the user, wherein the content includes user notification information containing or based on the high-priority sensor information identified from among the received sensor messages; and providing the audio voice message at the speaker of the ear-wearable device.

In a seventeenth aspect, in addition to one or more of the preceding or following aspects, or in the alternative to some aspects, the physiological sensor is located within a housing of the ear-wearable device.

In an eighteenth aspect, in addition to one or more of the preceding or following aspects, or in the alternative to some aspects, the physiological sensor includes a sensor housing separate from a housing of the ear-wearable device.

In a nineteenth aspect, in addition to one or more of the preceding or following aspects, or in the alternative to some aspects, the physiological sensor is a glucose sensor, a blood glucose sensor, a dehydration sensor, a temperature sensor, an inertial motion unit sensor, a gyroscope, an inertial measurement unit (IMU), a respiration rate sensor, an electrocardiogram sensor, a hormonal sensor, a fertility sensor, a blood pressure sensor, a peripheral capillary oxygen saturation sensor, a chemical sensor, a chemical blood sensor, a drug sensor, a voice pattern sensor, a stomach acidity sensor, a cholesterol level sensor, an implanted sensor, a pacemaker, or an electronic pill.

In a twentieth aspect, in addition to one or more of the preceding or following aspects, or in the alternative to some aspects, the system further can include a supplemental data source outputting supplemental data. The processor of the ear-wearable device or the processor of the gateway device is configured to: receive supplemental data from the supplemental data source; identify supplemental data from the supplemental data source relevant to the high-priority sensor information, wherein the content for the audio voice message includes supplemental data notification information containing or based on the identified supplemental data.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

A method and system is described herein for providing direct, informative, and high-priority notification messages to a user of an ear-wearable device system, such as a hearing aid, based on information about the user's body from physiological sensors worn by or attached to the user's body. The methods and systems described herein identify and provide high-priority notifications, such as time-sensitive notifications, directly to the user's hearing aid in the form of an audio voice message. For example, a user can be immediately informed using an audio voice message to the user's ear-wearable device that the user's blood glucose reading is low and the user should eat as soon as possible. In another example, a dehydration sensor detects if the user is dehydrated and the system informs the user that they should consume water or another form of hydration.

In some examples of high-priority messages, supplemental data is used to provide valuable information to the user that is relevant to the high-priority situation. For example, the system can access geo-location data of the user as a supplemental data source. Along with a blood glucose sensor warning, the system can provide information about the closest source of food, such as directions to a grocery store or restaurant.

In some examples, supplemental data is used to identify a high-priority message. In one such example, an inertial measurement unit (IMU) detects that the wearer has been exercising actively for an extended period of time and the system is also aware that there is a local environmental concern such as high humidity or an air quality alert because the system includes a gateway device that connects the system to a source of environmental information. The system informs the user to use caution and recommends taking a break.

In another example, a temperature sensor detects an elevated body temperature and an IMU detects that the user's activity level has been low, indicating that the elevated body temperature is unlikely to be exercise-related. The user is notified of the elevated body temperature and of the risk that they have contracted a virus or infection. The user can be provided with the location of or directions to the closest medical clinic.

In another example, a blood glucose sensor indicates a low or high level of blood glucose and the system is aware that the user is diabetic. The system can inform the user of the elevated or depressed glucose level so that the user is prompted to take their medication. In another example, a physiological sensor, such as a chemical sensor including a skin-mounted chemical sensor, detects the level of a medication in the user's system and has access to a supplemental data source providing a predicted level of medication in the user's system if they are taking their medication on the recommended schedule. The system can inform the user that their level of the medication does not match the expected level, and advise the user to check whether the medication was taken on schedule.

These are just a few examples of many high-priority notifications based on information from a physiological sensor that can be provided to a user of an ear-wearable device via a voice audio message according to the system and methods described herein.

Physiological sensors as that term is used herein means sensors that detect information about the condition of or movement of a user's body. Examples include a skin-mounted sensor, a glucose sensor, a blood glucose sensor, a dehydration sensor, a temperature sensor, an inertial motion unit sensor, a gyroscope, an inertial measurement unit (IMU), a respiration rate sensor, an electrocardiogram sensor, a hormonal sensor, a fertility sensor, a blood pressure sensor, a peripheral capillary oxygen saturation sensor, a chemical sensor, a chemical blood sensor, a drug sensor, a voice pattern sensor, a stomach acidity sensor, a cholesterol level sensor, an implanted sensor, a pacemaker, or an electronic pill. Examples of IMUs include inertial motion unit sensors and gyroscopes.

A user may have one, two, three, four, or more different devices worn on or carried on their body at one time, such as an ear-wearable device, a wrist-wearable device, a smart phone, a health sensor such as a glucose sensor, or other devices, that are able to provide information to one or more other devices. One or more of these devices may have a physiological sensor built into it. One or more of these devices may act as a gateway device to communication with a pervasive wireless network. In some example, an ear-wearable device includes one or more built-in physiological sensors. In some examples, the ear-wearable device acts as a gateway device. In some examples, the ear-wearable device is paired with a smart phone via wireless communication, and the smart phone acts as a gateway device.

The ear-wearable device system provides opportunities for the user to acknowledge high-priority messages in many different ways, including convenient, low-movement ways, such as hands-free methods. In some examples, a user can acknowledge a high-priority message by nodding their head, and that head nod is detected by an IMU of the ear-wearable device. In some examples, a user can acknowledge a high-priority message by tapping the ear-wearable device, and that tap is detected by an IMU of the ear-wearable device. In some examples, the user can acknowledge a high-priority message by pressing a button, tapping, touching a button on a screen of, or otherwise interfacing with a device that is a part of the system, such as a smart phone or wrist-wearable device.

Figure 1:
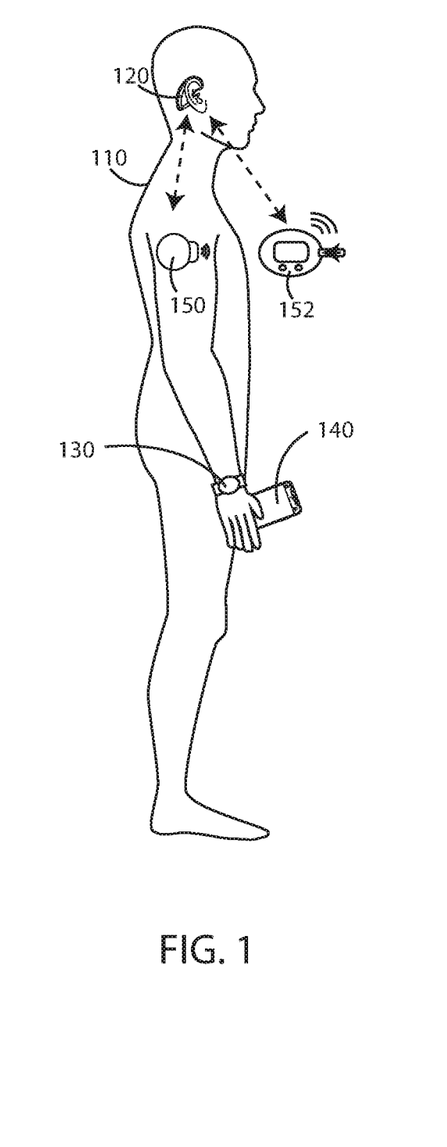
FIG. 1 is a schematic diagram of a user with an ear-wearable device, a wrist-wearable device having one or more physiological sensors, a skin-mounted sensor, another physiological sensor, and a gateway device, such as a cellular phone in accordance with various embodiments herein.
Figure 2:
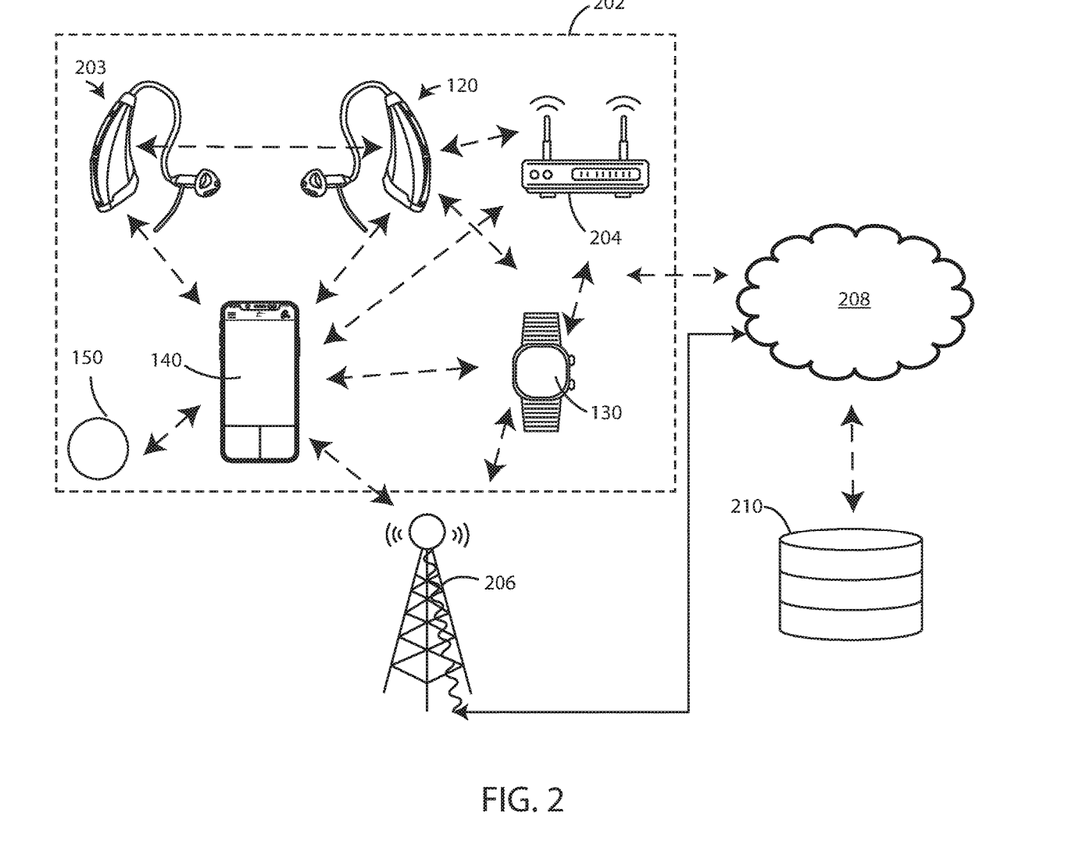
FIG. 2 is a schematic diagram of a system for providing high-priority notifications to a user including two ear-wearable devices, a wrist wearable device, and gateway in network communication with a data warehouse in accordance with various embodiments herein.

Ear-Wearable Device System (FIGS. 1-2)

FIG. 1 is a schematic diagram of an ear-wearable device system worn by a user 110. The system includes an ear-wearable device 120 and a wrist-wearable device 130, having one or more physiological sensors. The ear-wearable device 120 may itself incorporate physiological sensors in one of its housings, so that the physiological sensor is located within a housing of the ear-wearable device 120. The system also includes a smart phone 140 that is carried with the user, such as in the user's pocket. Either the ear-wearable device 120, the wrist-wearable device 130, or the smart phone 140 can act as a gateway device that communicates with a pervasive wireless network. The system can also include a skin-worn physiological sensor 150, such as a glucose sensor, chemical sensor, temperature sensor, hydration sensor, or sensor package, separate from the ear-wearable device 120 and the wrist-wearable device 130. In some embodiments, the system can include a physiological sensor that is an external device away from the skin, such as in the case of a test strip reader 152, which can analyze a sample of a bodily fluid such as blood for the presence and/or concentration of analytes such as glucose. Various other analytes are also contemplated herein.

FIG. 2 is a schematic diagram of a system for providing high-priority notifications to a user showing communication paths between components of the system and with a broader communications network. At a first location 202, the system includes a first ear-wearable device 120, a second ear-wearable device 203 for the user's other ear, a wrist-wearable device 130, and a smart phone 140. These components are configured to be worn by, carried by, or within the user. In some examples, either the ear-wearable device 120, the wrist-wearable device 130, or the smart phone 140 can act as a gateway device that communicates with a pervasive wireless network. The system at the first location 202 also includes a network router 204 which may also act as a gateway device. The gateway device includes a processor and a wireless communication device for communicating with a pervasive wireless network. If the gateway device is not the ear-wearable device 120, then the gateway device further comprises a wireless communication device for communicating with the ear-wearable device 120.

It will be appreciated that data and signals can be exchanged between many different components in accordance with embodiments herein. The system further include comprises a communications tower 206. Many different components at the first location 202 can act as a gateway device and communicate with the communication tower 206, such as a cellular tower, with the cloud 208, or via the cloud 208 to a data warehouse 210. The cloud 208 is a network of remote servers hosted on the Internet and used to store, manage, and process data. The cloud 208 can be a source of or a channel to supplemental data that can be useful to the system as a part of identifying high-priority messages and identifying content for the audio voice message.

The systems shown in FIGS. 1 and 2 can be used to provide high-priority notification messages to a user. The system includes a physiological sensor present on, within, or carried with the user, which can be built-into the ear-wearable device 120, the wrist-wearable device 130, or the smart phone 140. A skin-worn physiological sensor 150, such as a glucose sensor, can also be the sole physiological sensor of the system, or can be one of multiple physiological sensors of the system. The ear-wearable device includes a speaker for providing audio signals to the user's ear, a microphone for detecting audio signals close to the user, a processor, a memory storage, and a wireless communication device.

In one example, the processor of the ear-wearable device is capable of receiving a plurality of sensor messages from the one or more physiological sensors and identifying high-priority sensor information from among the plurality of received sensor messages. The processor is also capable of identifying content for an audio voice message to provide to the user, wherein the content comprises user notification information containing or based on the high-priority sensor information identified from among the received sensor messages. The processor is further capable of providing the audio voice message at the speaker of the ear-wearable device.

The physiological sensor can be located within a housing of the ear-wearable device. Alternatively or in addition, a physiological sensor can be included that has a sensor housing separate from a housing of the ear-wearable device.

In some embodiments, the system further includes a gateway device comprising a processor, a wireless communication device for communicating with the ear-wearable device, and a second wireless communication device for communicating with a pervasive wireless network. In embodiments including a gateway device, the processor of either the gateway device or the processor of the ear-wearable device, or both, can be configured to receive a plurality of sensor messages from the physiological sensor, identify high-priority sensor information from among the plurality of received sensor messages, and identify content for an audio voice message to provide to the user. The content for the audio voice message can include user notification information containing or based on the high-priority sensor information identified from among the received sensor messages. One of the processors can also be configured to provide the audio voice message at the speaker of the ear-wearable device.

Supplemental Data

In some examples, the system includes a supplemental data source that is configured to provide supplemental data as an input to the system. Supplemental data can be useful to the system as an input to the process of identifying high-priority messages. In addition or alternatively, supplemental data can be an input to the process of identifying content for the audio voice message. As used herein, supplemental data is data from sources other than a first physiological sensors. A second physiological sensor may be a source of supplemental data.

Examples of channels for receiving supplemental data are through a gateway device that is cloud connected or from a memory location of one of the devices at the first location. Examples of sources of supplemental data include databases accessible through the cloud 208. Examples of supplemental data in the cloud include weather data such as temperature, humidity, and weather forecasts for a specific geo-location from a weather database. Supplemental data can include environmental data for a specific geo-location, such as air quality data including air quality alerts, from an environmental database. Supplemental data can include the locations of businesses, such as restaurants and grocery stores, and what they sell or provide.

Another example of a source of supplemental data is one or more data warehouses 210. The data warehouse 210 can contain sensor data from the physiological sensors of the user aggregated over a period of time. The data warehouse can also include information about the user, such as the user's health conditions, biographical information, medications, and emergency contacts.

An example of supplemental data is the user's geographic location. An example of a source of supplemental data is a global positioning system (GPS) that can indicate the user's location. Data transmissions between a gateway device being held by, worn by, or in close proximity to the user and one or more communications towers or satellites can be used to ascertain the user's geographic location, also known as geo-location data.

In some examples of the system, the processor of the ear-wearable device or the processor of the gateway device is configured to receive supplemental data from the supplemental data source and identify supplemental data from the supplemental data source relevant to the high-priority sensor information. In some examples, the content for the audio voice message includes supplemental data notification information containing or based on the identified supplemental data.

Examples of supplemental data sources are a gateway device, a global positioning system, a calendar system, a personal contact information system, a contact directory system, a second physiological sensor, a database of user-selected parameters, a database of environmental information, a glucose sensor, a blood glucose sensor, a dehydration sensor, a temperature sensor, an inertial motion unit sensor, a gyroscope, an inertial measurement unit (IMU), a respiration rate sensor, an electrocardiogram sensor, a hormonal sensor, a fertility sensor, a blood pressure sensor, a peripheral capillary oxygen saturation sensor, a chemical sensor, a chemical blood sensor, a drug sensor, a voice pattern sensor, a stomach acidity sensor, a cholesterol level sensor, an implanted sensor, a pacemaker, or an electronic pill.

In various embodiments, data and/or signals can be exchanged directly between the first ear-wearable device 120, the second ear-wearable device 203, the smart phone 140, the wrist-wearable device 130, the network router 204, or subsets of these devices at the first location 202. Data and/or signals can be exchanged wirelessly using various techniques including inductive techniques (such as near-field magnetic induction—NFMI), 900 MHz communications, 2.4 GHz communications, communications at another frequency, FM, AM, SSB, BLUETOOTH™, Low Energy BLUETOOTH™, Long Range BLUETOOTH®, IEEE 802.11 (wireless LANs) wi-fi, 802.15 (WPANs), 802.16 (WiMAX), 802.20, and cellular protocols including, but not limited to CDMA and GSM, ZigBee, and ultra-wideband (UWB) technologies. Such protocols support radio frequency communications and some support infrared communications. It is possible that other forms of wireless communications can be used such as ultrasonic, optical, and others. It is understood that the standards which can be used include past and present standards. It is also contemplated that future versions of these standards and new future standards may be employed without departing from the scope of the present subject matter.

The system may include only one ear-wearable device or two ear-wearable devices. Each of the ear-wearable devices 120, 203 can include one or more built-in physiological sensors as described. The ear-wearable devices 120, 203 and sensors therein can be disposed on opposing lateral sides of the user's head. The ear-wearable devices 120, 203 and sensors therein can be disposed in a fixed position relative to the user's head. The ear-wearable devices 120, 203 and sensors therein can be disposed within opposing ear canals of the subject. The ear-wearable devices 120, 203 and sensors therein can be disposed on or in opposing ears of the user. The ear-wearable devices 120, 203 and sensors therein can be spaced apart from one another by a distance of at least 3, 4, 5, 6, 8, 10, 12, 14, or 16 centimeters and less than 40, 30, 28, 26, 24, 22, 20 or 18 centimeters, or by a distance falling within a range between any of the foregoing.

Figure 3:
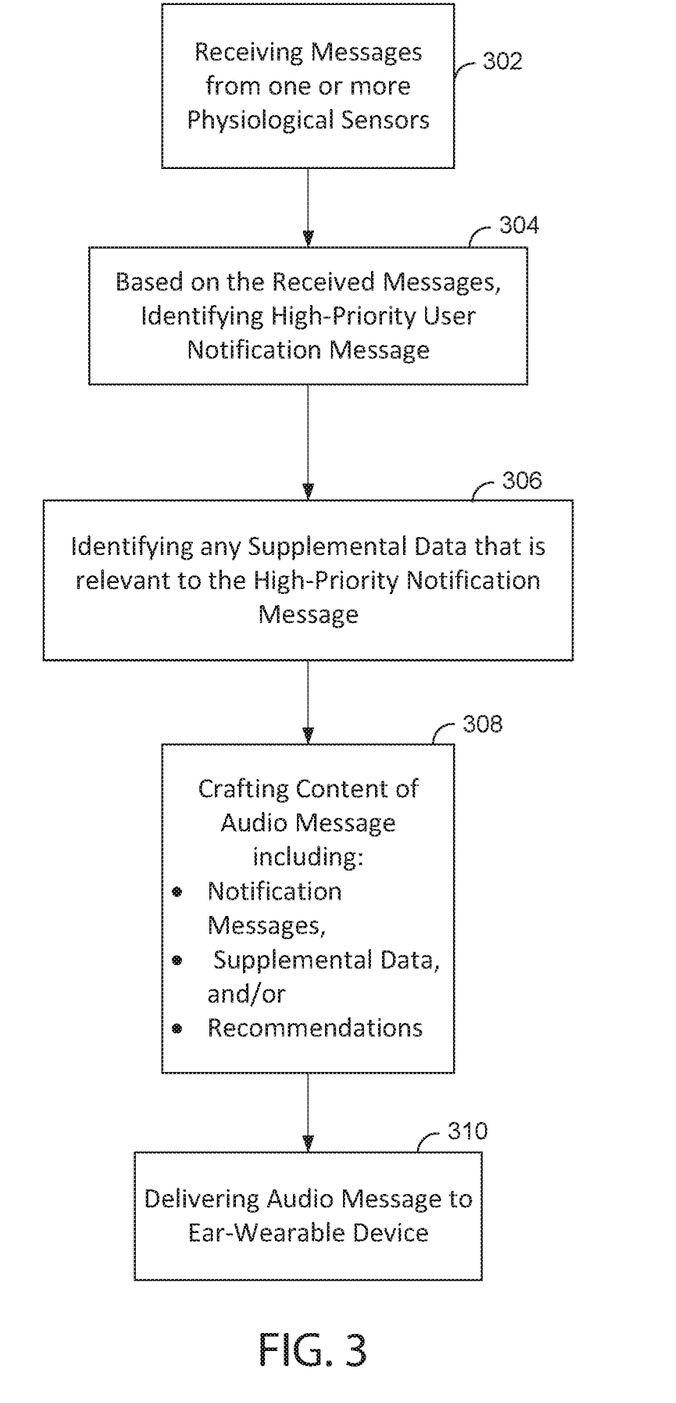
FIG. 3 is a flowchart of a method for providing high-priority notification messages to a user of a system including an ear-wearable device in accordance with various embodiments herein.

Method of Providing High-Priority Notification Messages (FIG. 3)

Now referring to FIG. 3, a flowchart of one method for providing high-priority notification messages to a user of a system including an ear-wearable device is shown. In one example, a method for providing high-priority notification messages to a user of an ear-wearable device system operates where the system includes a physiological sensor present on, within, or carried with the user and an ear-wearable device comprising a speaker, a microphone, a processor, a memory storage, and a wireless communication device. A first step 302 is receiving sensor messages from one or more physiological sensors. These messages may be received by a processor of the ear-wearable device, a processor of a smart phone device, or by a processor of another device in the system.

At step 304, based on the received sensor messages, high-priority sensor information is identified from among the plurality of received sensor messages. The definition of high-priority sensor information can be set as a default in the system without any user intervention. In some examples, certain aspect of or all aspects of the definition of high-priority sensor information can be catered for a particular user, such as selected by a particular user. An example of high-priority sensor information includes a blood glucose sensor reading that is low, such as below a threshold. Another example of high-priority sensor information is a reading from a dehydration sensor that indicates that the user is dehydrated. Another example of a high-priority sensor information is a body temperature reading above a threshold or below a threshold.

In some methods, supplemental data can be used to identify if a particular piece of sensor information is high-priority sensor information. In the absence of the supplemental data, it may be unclear whether a particular piece of sensor data is high-priority or not. In some methods, as indicated at step 306, the system identifies supplemental data that is relevant to the high-priority notification message. The supplemental data may be relevant because it indicates that the sensor information is high-priority. The supplemental data may also be relevant because it can be used to improve the information provided to the user in the content of the audio message.

Examples of supplemental data that can be relevant to the sensor information include geo-location data, user health information, environmental data, and weather data, among other types of data. In one such example, an inertial measurement unit (IMU) is a physiological sensor that detects that the wearer has been exercising actively for an extended period of time. The system can access a user's geo-location data as a first source of supplemental data, and then access an environmental database and a weather database as a second source of supplemental data to check if there is a local environmental concern such as high humidity or an air quality alert at the user's geo-location. A gateway device can connect the system to the weather database or environmental database. In this example, the system can craft a message informing the user to use caution and recommending a break.

In another example of supplemental data being used to identify high-priority sensor information, a temperature sensor is a first physiological sensor that detects an elevated body temperature and an IMU is a physiological sensor that is a source of supplemental data that detects that the user's activity level has been low. This combination of two types of sensor information indicates that the elevated body temperature is unlikely to be exercise-related, and as a result that the sensor information is high-priority sensor information. The system can craft a message notifying the user of the elevated body temperature and of the risk that they have contracted a virus or infection.

In another example, a blood glucose sensor is a first physiological sensor that collects sensor data indicating a low or high level of blood glucose and the system has access to a data warehouse containing supplemental information including user information indicating that the user is diabetic. The system can create message content to inform the user of the elevated or depressed glucose level so that the user is prompted to take their medication. In another example, a first physiological sensor is a chemical sensor that detects the level of a medication in the user's system and has access to a supplemental data source such as a data warehouse providing a predicted level of medication in the user's system if they are taking their medication on the recommended schedule. The system can craft a message to inform the user that their level of the medication does not match the expected level, and advise the user to check whether the medication was taken on schedule.

In step 308, the system identifies content for an audio voice message to provide to the user. The content may include user notification information containing or based on the high-priority sensor information identified from among the received sensor messages, as discussed in a number of examples herein. The content may also include supplemental data notification information containing or based on the supplemental data. The content may also include recommendations to the user.

One example of content for an audio voice message is directions to a location relevant to the high-priority sensor information. For example, the system can have access to geo-location data of the user as supplemental data from a GPS as a supplemental data source. The system can also have access to a database of businesses and the products and services that they provide, linked to geo-location data of the businesses, as a supplemental data source.

In step 310, the system delivers the audio voice message at the speaker of the ear-wearable device. In various examples of the system, the user is provided with the audio voice message, including or based on the high-priority sensor information, without being required to interface with a device. As a result, it is more likely that the user will receive the high-priority message than if the user were required to interface with a device to receive the information.

In some methods, the system sends the plurality of sensor messages to a data warehouse location. The system can analyze the plurality of sensor messages received at the data warehouse location for trends using analysis techniques. The system can perform machine learning training to improve the techniques used to analyze the plurality of sensor messages received at the data warehouse location.

In one example method, the system receives input from the user of the ear-wearable device system at the data warehouse location to facilitate identifying high-priority sensor information. For example, the user can provide health information, such as the user being diabetic, a normal body temperature range for the user, a normal blood glucose level range for the user, and typical activity profiles for the user. The user-provided information is then applied to improve the analysis techniques. The user-provided information can be feedback or reaction to a high-priority notification.

The content of the audio voice message can be crafted by the system using user configuration choices as input. In some examples, the user can select whether to hear a recommendation along with a time-sensitive notification, or to only hear the time-sensitive notification. In addition or alternatively, if the content of a notification or a recommendation will include geo-location data, such as where the user could travel to meet their needs, there are a variety of ways that geo-location data could be provided. The user can select in a configuration profile how they want to receive geo-location data, such as selecting between geo-location format examples include providing turn-by-turn directions at the time of the notification or simply providing the name of the location and an address of the location without turn-by-turn directions.

Figure 4:
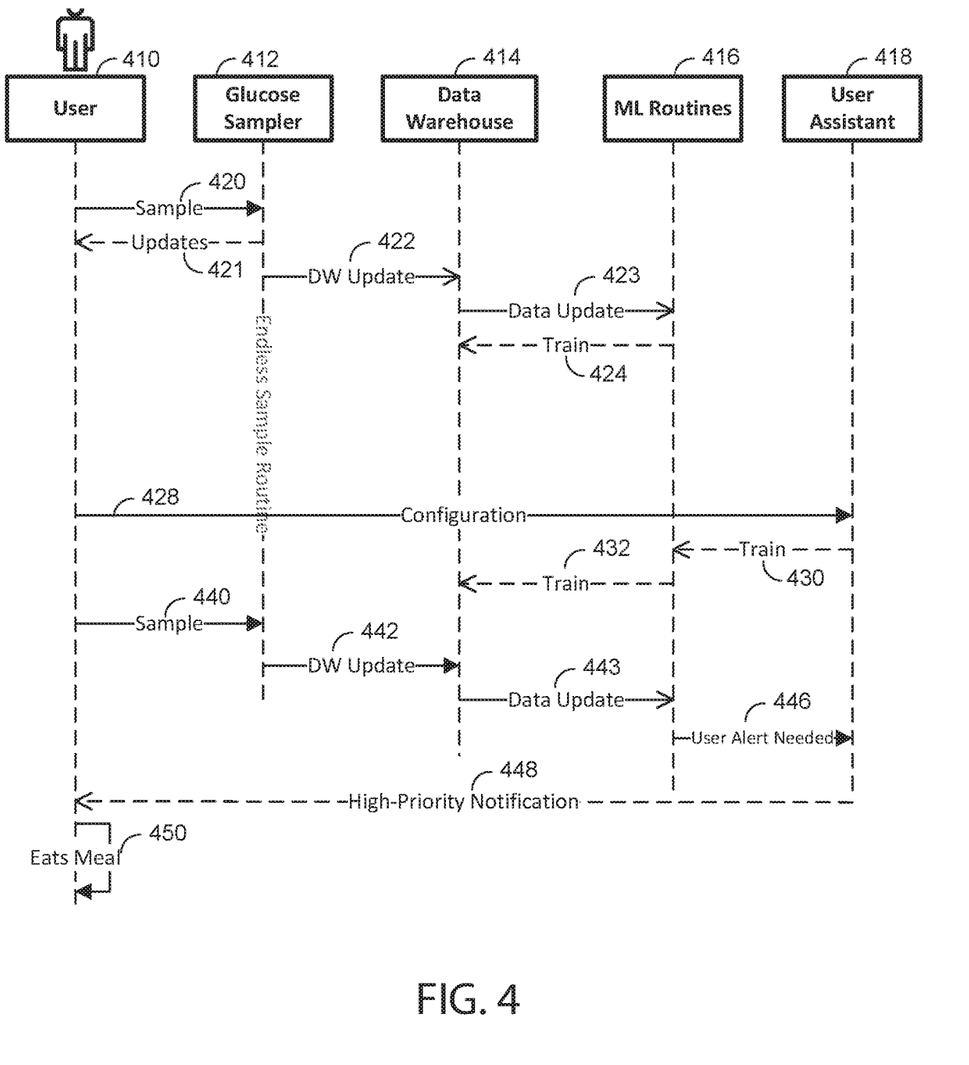
FIG. 4 is a data flow diagram for a glucose monitoring system for generating high-priority notifications to a user of a system including an ear-wearable device in accordance with various embodiments herein.

Data Flow for Data from a Physiological Sensor (FIG. 4)

FIG. 4 is a data flow diagram for a glucose monitoring system for generating high-priority, time-sensitive notifications to a user of a system including an ear-wearable device.

A change in time is indicated by the flow of the diagram from top to bottom. FIG. 4 shows data flow between a user 410, a glucose sampler 412, a data warehouse 414, machine learning routines 416, and a user assistant system 418, moving from left to right across the diagram. The user assistant system 418 can be a computer program system or application system. The user assistant system 418 can include a user interface, such as an interface of an application on a smart phone, and can interface with the data warehouse and the machine learning routines. The concepts discussed with respect to FIG. 4 are relevant to many other types of sensor information in addition to information from a glucose sensor.

Physiological sensors interact with the patient to gather sensor information. In the example of FIG. 4, the user 410 provides a first sample 420 to the glucose sampler 412. The glucose sampler 412 can provide updates 421 to the devices at the location of the user 410. Examples of updates 421 include configuration changes and retrained artificial intelligence algorithms.

The glucose sampler 412 provides a data warehouse update 422 to the data warehouse 414, containing the glucose reading and user-identifying information. The data warehouse update 422 may also include a time of the sample and other information.

The data warehouse 414 stores the information provided in the data warehouse update 422 in a computer readable memory location. The data warehouse 414 also provides a data update 423 to machine learning routines 416. As a result of receiving the data update 423, the machine learning routines 416 may output training information 424 to the data warehouse 414. The training information may assist a process at the data warehouse 414 with identifying high-priority sensor information from among the plurality of sensor messages received. In the example of sample 420, the sensor message or data warehouse update 422 was provided to all system components and did not result in a high-priority notification being generated.

FIG. 4 also illustrates that a configuration update 428 can be provided to the user assistant system 418. The configuration update 428 can be a result of machine learning by one of the user devices or can be a result of a direct user choice. Examples of configuration updates 428 that may be provided by the user as a user choice include choosing that a specific glucose reading would trigger a high-priority notification, choosing that a specific glucose reading would not trigger a high-priority notification, or other configurations. The configuration update 428 to the user assistant system 418 results in training update 430 to the machine learning routines 416 and training update 432 to the data warehouse 414.

At a point in time later than first sample 420, the user 410 provides a second sample 440 to the glucose sampler 412. The glucose sampler 412 provides a data warehouse update 442 to the data warehouse 414. The data warehouse 414 stores the information provided in the data warehouse update 442 in a computer readable memory location. The data warehouse 414 also provides a data update 443 to machine learning routines 416. As a result of receiving the data update 423, the machine learning routines 416 determines that a user alert 446 is appropriate and pushes that information to the user assistant 418. As a result, a high-priority notification 448 is provided to the user 410. For example, the system may deliver an audio voice message to the user stating that the blood glucose level requires attention, directing the user to eat a meal, and advising the user of the location of a nearby restaurant.

Depending on the user's configuration choices, the system may only provide the notification that the blood glucose needs attention. Depending on the user's configuration choices, the system may provide the notification that the blood glucose needs attention along with geo-location data regarding a location where food can be obtained, such as a restaurant or grocery store. The geo-location data provided may simply be an address or can be turn-by-turn directions. Next, having been notified that eating is important, the user eats a meal 450 to address the subject of the notification.

The system is configured to send sensor messages, also referred to as data warehouse updates 422, to a data warehouse location 414. In some embodiments, the data warehouse updates 422 received at the data warehouse location 414 are analyzed for trends using analysis techniques. In some embodiments, machine learning training 416 is performed to improve the analysis techniques used to analyze the data warehouse updates 422.

The functions of machine learning, user assistant, data warehouse, or a combination of these can be provided in the cloud. Alternatively, these functions or combinations of these can be provided in other locations and/or on other devices, such on a gateway device, a smart phone, or on an ear-wearable device.

Acknowledgement of a High-Priority Notification

The system can be configured to receive an acknowledgement of a high-priority notification from the user. The system can be configured to repeat a high-priority notification at intervals until receiving an acknowledgement from a user. In some examples, the user can configure the system regarding whether the system takes any action based on whether an acknowledgement is received, such as repeating the notification, the intervals of repetition, and/or the methods of acknowledgement by the user.

Examples of the ear-wearable device system provide opportunities for the user to acknowledge high-priority messages in many different ways, including hands-free methods. In a hands-free example, a user can acknowledge a high-priority message by moving their head, and movement is detected by an IMU of the ear-wearable device. Examples of head movement that can be detected include nodding, shaking side-to-side, or nodding twice. In some examples, a user can acknowledge a high-priority message by tapping the ear-wearable device, and that tap is detected by an IMU of the ear-wearable device. In some examples, a user can acknowledge a high-priority message by tapping the user's head or ear, and that tap is detected by an IMU of the ear-wearable device. The tap can be a single tap, double tap, triple tap, or have another particular pattern or sequence. In some examples, the user can acknowledge a high-priority message by pressing a button, tapping, touching a button on a screen of, or otherwise interfacing with a device that is a part of the system, such as a smart phone or wrist-wearable device.

In some examples of the system, the user can acknowledge a high-priority message by speaking and the system will listen for a user response. In one example, a user can acknowledge a high-priority message by speaking a predetermined phrase that the system will detect, such as, "Got it," "Acknowledged." "Yes." "I know," or "Understood." In some examples of the system, the system can listen for a response to a query, such as, "Yes," "No," or "Tell me more."

In some examples of the system, the user can acknowledge a high-priority message by a body motion such as a hand motion that is detected by a sensor of the system. In one example, a user can acknowledge a high-priority message by waving a hand. In one example, a user can acknowledge a high-priority message by making an okay sign or another sign with the user's hand. A camera can be included in the system to detect such body motions. A wrist-worn sensor can be configured to detect a hand motion or other types of body motions.

Figure 5:
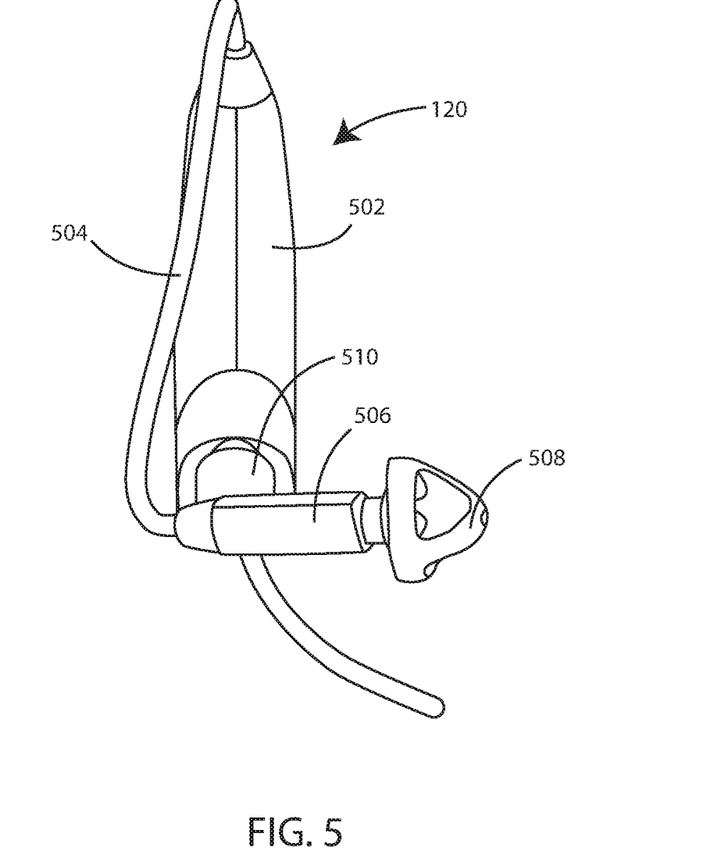
FIG. 5 is a schematic view of an ear-wearable device in accordance with various embodiments herein.
Figure 6:
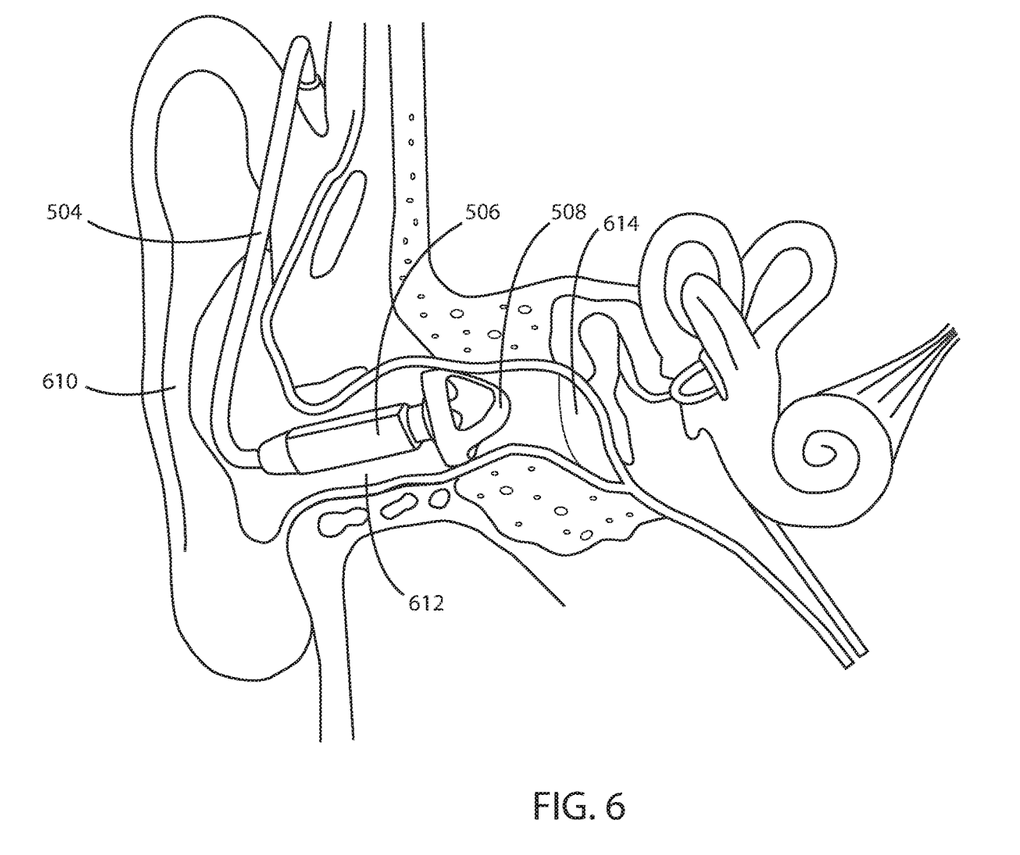
FIG. 6 is a schematic view of an ear-wearable device partially placed within the ear canal of a subject in accordance with various embodiments herein.
Figure 7:
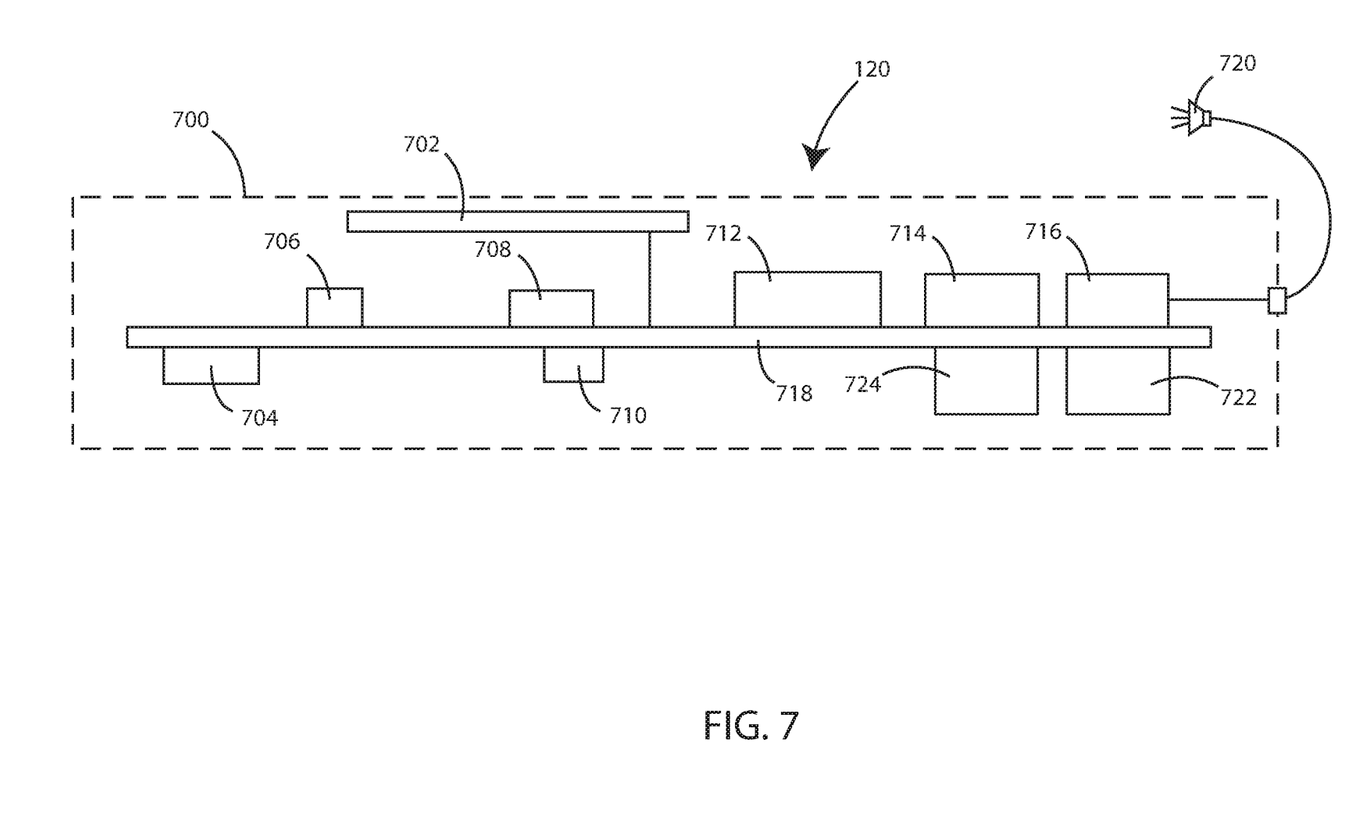
FIG. 7 is a schematic view of components of an ear-wearable device in accordance with various embodiments herein.

Ear-Wearable Devices (FIGS. 5-7)

Referring now to FIG. 5, a schematic view of an ear-wearable device 120 is shown in accordance with various embodiments herein. The ear-wearable device 120 can include a device housing 502. The device housing 502 can define a battery compartment 510 into which a battery can be disposed to provide power to the device. The ear-wearable device 120 can also include a receiver 506 adjacent to an earbud 508. The receiver 506 can include a component that converts electrical impulses into sound, such as an electroacoustic transducer, speaker, or loud speaker. A cable 504 or connecting wire can include one or more electrical conductors and provide electrical communication between components inside of the device housing 502 and components inside of the receiver 506.

Referring now to FIG. 6, a schematic view is shown of an ear-wearable device partially disposed within the ear canal 612 of a subject in accordance with various embodiments herein. In this view, the receiver 506 and the earbud 508 are both within the ear canal 612, but do not directly contact the tympanic membrane 614. The device housing is mostly obscured in this view behind the pinna 610, but it can be seen that the cable 504 passes over the top of the pinna 610 and down to the entrance to the ear canal 612.

Referring now to FIG. 7, a schematic block diagram is shown with various components of an ear-wearable device 120 in accordance with various embodiments. The block diagram of FIG. 7 represents a generic ear-wearable device for purposes of illustration. The ear-wearable device 120 can include several components electrically connected to a mother circuit 718 (e.g., flexible or non-flexible mother board) which is disposed within housing 700. A power supply circuit 704 can include a battery and can be electrically connected to the mother circuit 718 and provides power to the various components of the ear-wearable device 120. One or more microphones 706 are electrically connected to the mother circuit 718, which provides electrical communication between the microphones 706 and a digital signal processor (DSP) 712, as well as to other components. Among other components, the DSP 712 incorporates or is coupled to audio signal processing circuitry configured to implement various functions described herein. A sensor package 714 can be coupled to the DSP 712 via the mother circuit 718. The sensor package 714 can include one or more different specific types of sensors such as those described in greater detail below. In some embodiments, one or more user switches 710 (e.g., on/off, volume, mic directional settings) are electrically coupled to the DSP 712 via the mother circuit 718.

An audio output device 716 is electrically connected to the DSP 712 via the mother circuit 718. In some embodiments, the audio output device 716 comprises a speaker (coupled to an amplifier). In other embodiments, the audio output device 716 comprises an amplifier coupled to an external receiver 720 adapted for positioning within an ear of a wearer. The external receiver 720 can include an electroacoustic transducer, speaker, or loud speaker. The ear-wearable device 120 may incorporate a wireless communication device 708 coupled to the mother circuit 718 and to an antenna 702 directly or indirectly via the mother circuit 718. The communication device 708 can be a BLU- ETOOTH® transceiver, such as a BLE (BLUETOOTH® low energy) transceiver or other transceiver (e.g., an IEEE 802.11 compliant device). The communication device 708 can be configured to communicate with one or more other devices of the system, in accordance with various embodiments. In various embodiments, the communication device 708 can be configured to communicate with a gateway device, a physiological sensor, a smart phone, a wrist-worn device, a video display screen, a tablet, a computer, a virtual reality display device, an augmented reality display device, or the like.

In various embodiments, the ear-wearable device 120 can also include a control circuit 722 and a memory storage device 724. The control circuit 722 can be in electrical communication with other components of the device. The control circuit 722 can execute various operations, such as those described herein. The control circuit 722 can include various components including, but not limited to, a microprocessor, a microcontroller, an FPGA (field-programmable gate array) processing device, an ASIC (application specific integrated circuit), or the like. The term control circuit can be used interchangeably with processor. The memory storage device 724 can include both volatile and non-volatile memory. The memory storage device 724 can include ROM, RAM, flash memory, EEPROM, SSD devices, NAND chips, and the like. The memory storage device 724 can be used to store data from sensors as described herein and/or processed data generated using data from sensors as described herein.

Physiological Sensors

Physiological sensors as that term is used herein means sensors that detect information about the condition of or movement of a user's body. Examples include a glucose sensor, a blood glucose sensor, a dehydration sensor, a temperature sensor, an inertial motion unit sensor, a gyroscope, an inertial measurement unit (IMU), a respiration rate sensor, an electrocardiogram sensor, a hormonal sensor, a fertility sensor, a blood pressure sensor, a peripheral capillary oxygen saturation sensor, a chemical sensor, a chemical blood sensor, a drug sensor, a voice pattern sensor, a stomach acidity sensor, a cholesterol level sensor, an implanted sensor, a pacemaker, or an electronic pill. Examples of IMUs include inertial motion unit sensors and gyroscopes.

Some examples of physiological sensors include skin contact devices configured for contact with the skin of the user. In some embodiments, the skin contact device could be a skin-mounted sensor device 150 such as a glucose sensor. In some embodiments, the skin contact device can be a skin-mounted patch, including, but not limited to, a transdermal drug delivery patch or a skin-mounted sensor patch. An exemplary skin-mounted sensor patch can include a skin-mounted glucose sensor and/or a skin-mounted blood pressure sensor such as a blood pressure monitoring patch. In various embodiments, a medical device herein (such as a skin-mounted device) can include a glucose sensor such as a continuous glucose monitor (CGM), such as a G6 CGM system commercially available from Dexcom, a LIBRE CGM system commercially available from Abbott, or a GUARDIAN Connect CGM system commercially available from Medtronic. Exemplary CGM devices include those described in U.S. Pat. Nos. 9,452,259, and 7,920,907, and U.S. Publ. Pat. Appl. No. 2019/0041345, the content of which is herein incorporated by reference.

Other skin-mounted sensors and/or sensor patches can include hydration sensors. Exemplary hydration and sweat sensing sensors and systems can include those described in U.S. Publ. Pat. Appl. Nos. 2015/0057515, 2018/0263538, 2019/0059795, 2017/0172484, 2018/0344223, 2018/0035928, and U.S. Pat. Nos. 10,136,831 and 9,867,539, the content of all of which are herein incorporated by reference.

Physiological sensors can also include discrete or integrated sensors to provide data. In some examples, a sensor package can comprise one or a multiplicity of sensors. In some embodiments, the sensors can include one or more motion sensors amongst other types of sensors. Motion sensors herein can include inertial measurement units (IMU), accelerometers, gyroscopes, barometers, altimeters, and the like. Motions sensors can be used to track movement of a user in accordance with various embodiments herein.

In some embodiments, an IMU can be disposed in a fixed position with respect to the head of a patient, such as worn on or near the head or ears. In some embodiments, an IMU can be worn on or near another part of the body such as on a wrist, arm, or leg of the patient.

According to various embodiments, a sensor package can include one or more of an IMU, and accelerometer (3, 6, or 9 axis), a gyroscope, a barometer, an altimeter, a magnetometer, a magnetic sensor, an eye movement sensor, a pressure sensor, an acoustic sensor, a telecoil, a heart rate sensor, a global positioning system (GPS), a temperature sensor, a blood pressure sensor, an oxygen saturation sensor, an optical sensor, a blood glucose sensor (optical or otherwise), a galvanic skin response sensor, a cortisol level sensor (optical or otherwise), a microphone, acoustic sensor, an electrocardiogram (ECG) sensor, electroencephalography (EEG) sensor which can be a neurological sensor, eye movement sensor (e.g., electrooculogram (EOG) sensor), myographic potential electrode sensor (EMG), a heart rate monitor, a pulse oximeter, a wireless radio antenna, blood perfusion sensor, hydrometer, sweat sensor, cerumen sensor, air quality sensor, pupillometry sensor, cortisol level sensor, hematocrit sensor, light sensor, image sensor, and the like.

In some embodiments, the sensor package can be part of an ear-wearable device. However, in some embodiments, the sensor packages can include one or more additional sensors that are external to an ear-wearable device. For example, various of the sensors described above can be part of a wrist-worn or ankle-worn sensor package, or a sensor package supported by a chest strap.

Data produced by a physiological sensor or the physiological sensors of a sensor package can be operated on by a processor of the device or system.

As used herein the term "inertial measurement unit" or "IMU" shall refer to an electronic device that can generate signals related to a body's specific force and/or angular rate. IMUs herein can include one or more accelerometers (3, 6, or 9 axis) to detect linear acceleration and a gyroscope to detect rotational rate. In some embodiments, an IMU can also include a magnetometer to detect a magnetic field.

The eye movement sensor may be, for example, an electrooculographic (EOG) sensor, such as an EOG sensor disclosed in commonly owned U.S. Pat. No. 9,167,356, which is incorporated herein by reference. The pressure sensor can be, for example, a MEMS-based pressure sensor, a piezo-resistive pressure sensor, a flexion sensor, a strain sensor, a diaphragm-type sensor and the like.

In some embodiments, the system can include a physiological sensor that is an external device away from the skin, such as in the case of a test strip reader, which can analyze a sample of a bodily fluid such as blood for the presence and/or concentration of analytes such as glucose.

The temperature sensor can be, for example, a thermistor (thermally sensitive resistor), a resistance temperature detector, a thermocouple, a semiconductor-based sensor, an infrared sensor, or the like. The blood pressure sensor can be, for example, a pressure sensor. The heart rate sensor can be, for example, an electrical signal sensor, an acoustic sensor, a pressure sensor, an infrared sensor, an optical sensor, or the like. The oxygen saturation sensor (such as a blood oximetry sensor) can be, for example, an optical sensor, an infrared sensor, or the like. The electrical signal sensor can include two or more electrodes and can include circuitry to sense and record electrical signals including sensed electrical potentials and the magnitude thereof (according to Ohm's law where V=IR) as well as measure impedance from an applied electrical potential.

It will be appreciated that a physiological sensor or a sensor package can include one or more sensors that are external to the hearing assistance device. In addition to the external sensors discussed hereinabove, the sensor package can comprise a network of body sensors (such as those listed above) that sense movement of a multiplicity of body parts (e.g., arms, legs, torso). In some embodiments, the hearing assistance device can be in electronic communication with the sensors or processor of another medical device, e.g., an insulin pump device or a heart pacemaker device.

Gateway Devices

One example of a gateway device is a smart phone, but many other devices can serve as gateway devices. In some examples, a gateway device includes a processor, a wireless communication device for communicating with the ear-wearable device, and a second wireless communication device for communicating with a pervasive wireless network. In some examples, the gateway device includes a visual display screen, a touch screen, and a number of user input buttons, such as a power button, volume buttons, a home button, and a sleep button. The gateway device may have access to network resources, such as a cellular network or another wide area network. The gateway device has the ability to communicate wirelessly with the ear-wearable device. Examples of a gateway device include a smart phone, wrist-worn device, computer tablet, laptop computer, cellular telephone, personal digital assistant, personal computer, streaming device, wide area network device, personal area network device, remote microphone, smart watch, home monitoring device, internet gateway, hearing device programmer, smart glasses, a captioning device, and combinations thereof, or the like. Hardware components consistent with various gateway devices are described in U.S. Publ. Appl. No. 2018/0341582 titled USER DEVICE INCLUDING A NONVOLATILE MEMORY DEVICE AND A DATA WRITE METHOD THEREOF, the content of which is herein incorporated by reference.

Data and/or signals can be exchanged between the gateway device and one or both of the hearing assistance devices (as well as from a gateway device to another location or device) using various techniques including, but not limited to inductive techniques (such as near-field magnetic induction—NFMI), 900 MHz communications, 2.4 GHz communications, communications at another frequency. FM, AM, SSB, BLUETOOTH™, Low Energy BLUETOOTH™, Long Range BLUETOOTH™, IEEE 802.11 (wireless LANs) Wi-Fi, 802.15 (WPANs), 802.16 (WiMAX), 802.20, and cellular protocols including, but not limited to CDMA and GSM, ZigBee, and ultra-wideband (UWB) technologies. Such protocols support radio frequency communications and some support infrared communications. It is possible that other forms of wireless communications can be used such as ultrasonic, optical, and others. It is also possible that forms of wireless mesh networks may be utilized to support communications between various devices, including devices worn by other individuals. It is understood that the standards which can be used include past and present standards. It is also contemplated that future versions of these standards and new future standards may be employed without departing from the scope of the present subject matter.

The gateway device can also exchange data across a data network to the cloud, such as through a wireless signal connecting with a local gateway device, such as over a mesh network, such as a network router or through a wireless signal connecting with a communications tower or similar communications tower. In some embodiments, the gateway device can also connect to a data network to provide communication to the cloud through a direct wired connection.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A method for providing high-priority notification messages to a user of an ear-wearable device system comprising one or more physiological sensors and an ear-wearable device, the method comprising:

receiving a plurality of sensor messages from the one or more physiological sensors;

identifying whether there is any high-priority sensor information from among the plurality of received sensor messages;

if high-priority sensor information is identified from among the plurality of received sensor messages, then identifying content for an audio voice message containing or based on the high-priority sensor information to provide to the user; and providing the audio voice message at a speaker of the ear-wearable device.

2. The method of claim 1 wherein the one or more physiological sensors are located within a housing of the ear-wearable device.

3. The method of claim 1 wherein the one or more physiological sensors comprise a sensor housing separate from a housing of the ear-wearable device.

4. The method of claim 1 wherein the one or more physiological sensors comprise a glucose sensor, a blood glucose sensor, a dehydration sensor, a temperature sensor, an inertial motion unit sensor, a gyroscope, an inertial measurement unit (IMU), a respiration rate sensor, an electrocardiogram sensor, a hormonal sensor, a fertility sensor, a blood pressure sensor, a peripheral capillary oxygen saturation sensor, a chemical sensor, a chemical blood sensor, a drug sensor, a voice pattern sensor, a stomach acidity sensor, a cholesterol level sensor, an implanted sensor, a pacemaker, or an electronic pill.

5. The method of claim 1 wherein the plurality of sensor messages are received by a processor of the ear-wearable device.

6. The method of claim 1 wherein the ear-wearable device system further comprises a gateway device, the gateway device comprising a processor, a wireless communication device for communicating with the ear-wearable device, and a second wireless communication device for communicating with a pervasive wireless network, wherein the plurality of sensor messages are received by the processor of the gateway device.

7. The method of claim 1 further comprising:

sending the plurality of sensor messages to a data warehouse location;

analyzing the plurality of sensor messages received at the data warehouse location for trends using one or more analysis techniques;

performing machine learning training to improve the one or more analysis techniques used to analyze the plurality of sensor messages received at the data warehouse location;

receiving, at the data warehouse location, first input from the user of the ear-wearable device system; and applying the first input to improve the one or more analysis techniques.

8. The method of claim 1 further comprising identifying supplemental data from a supplemental data source relevant to the high-priority sensor information, wherein the content for the audio voice message comprises supplemental data notification information containing or based on the supplemental data.

9. The method of claim 8 wherein the supplemental data is geo-location data and the supplemental data source is a global positioning system.

10. The method of claim 9 wherein the supplemental data is directions to a location relevant to the high-priority sensor information.

11. The method of claim 8 wherein the supplemental data source is a gateway device, a global positioning system, a calendar system, a personal contact information system, a contact directory system, a second physiological sensor, a database of user-selected parameters, a database of environmental information, a glucose sensor, a blood glucose sensor, a dehydration sensor, a temperature sensor, an inertial motion unit sensor, a gyroscope, an inertial measurement unit (IMU), a respiration rate sensor, an electrocardiogram sensor, a hormonal sensor, a fertility sensor, a blood pressure sensor, a peripheral capillary oxygen saturation sensor, a chemical sensor, a chemical blood sensor, a drug sensor, a voice pattern sensor, a stomach acidity sensor, a cholesterol level sensor, an implanted sensor, a pacemaker, or an electronic pill.

12. The method of claim 1 wherein a definition of the high-priority sensor information is set as a default in the ear-wearable device system without any intervention by the user.

13. An ear-wearable device system capable of providing high-priority notification messages to a user, comprising:

a physiological sensor present on, within, or carried with the user; and an ear-wearable device comprising a speaker, a microphone, a processor, a memory storage, and a wireless communication device, wherein the processor is configured to:

receive a plurality of sensor messages from the physiological sensor;

identify whether there is any high-priority sensor information from among the plurality of received sensor messages;

if high-priority sensor information is identified from among the plurality of received sensor messages, then identify content for an audio voice message to provide to the user, wherein the content comprises user notification information containing or based on the high-priority sensor information identified from among the plurality of received sensor messages; and provide the audio voice message at the speaker of the ear-wearable device.

14. The system of claim 13 wherein the physiological sensor is located within a housing of the ear-wearable device.

15. The system of claim 13 wherein the physiological sensor comprises a sensor housing separate from a housing of the ear-wearable device.

16. The system of claim 13 wherein the physiological sensor is a glucose sensor, a blood glucose sensor, a dehydration sensor, a temperature sensor, an inertial motion unit sensor, a gyroscope, an inertial measurement unit (IMU), a respiration rate sensor, an electrocardiogram sensor, a hormonal sensor, a fertility sensor, a blood pressure sensor, a peripheral capillary oxygen saturation sensor, a chemical sensor, a chemical blood sensor, a drug sensor, a voice pattern sensor, a stomach acidity sensor, or a cholesterol level sensor, an implanted sensor, a pacemaker, or an electronic pill.

17. A method for providing high-priority notification messages to a user of an ear-wearable device system comprising one or more physiological sensors and an ear-wearable device, the method comprising:

receiving a plurality of sensor messages from the one or more physiological sensors;

identifying high-priority sensor information from among the plurality of received sensor messages;

identifying content for an audio voice message containing or based on the high-priority sensor information to provide to the user;

providing the audio voice message containing or based on the high-priority sensor information at a speaker of the ear-wearable device; and recognizing acknowledgement of the audio voice message containing or based on the high-priority sensor information by the user.

18. The method of claim 17 wherein recognizing acknowledgement of the audio voice message containing or based on the high-priority sensor information by the user includes detecting a nodding motion of the user's head.

19. The method of claim 17 wherein recognizing acknowledgement of the audio voice message containing or based on the high-priority sensor information by the user includes detecting one or more user taps on the ear-wearable device.

20. The method of claim 17 wherein recognizing acknowledgement of the audio voice message containing or based on the high-priority sensor information by the user includes detecting user interaction with a smart phone or a wrist-wearable device.

* * * * *